United States Patent
Park et al.

(10) Patent No.: US 9,994,652 B2
(45) Date of Patent: Jun. 12, 2018

(54) METALLOCENE COMPOUND, CATALYST COMPOSITION INCLUDING THE SAME, AND METHOD OF PREPARING POLYOLEFIN USING THE SAME

(71) Applicant: LG CHEM, LTD., Seoul (KR)

(72) Inventors: Jin Young Park, Daejeon (KR); Yong Ho Lee, Daejeon (KR); Kyung Jin Cho, Daejeon (KR); Ki Soo Lee, Daejeon (KR); Bog Ki Hong, Daejeon (KR); Min Seok Cho, Daejeon (KR); Dae Hwan Kim, Daejeon (KR); Se Young Kim, Daejeon (KR); Sung Min Lee, Daejeon (KR); Chang Woan Han, Daejeon (KR); Sung Ho Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days. days.

(21) Appl. No.: 15/316,829

(22) PCT Filed: Jan. 28, 2015

(86) PCT No.: PCT/KR2015/000926
§ 371 (c)(1),
(2) Date: Dec. 6, 2016

(87) PCT Pub. No.: WO2016/122018
PCT Pub. Date: Aug. 4, 2016

(65) Prior Publication Data
US 2017/0107307 A1    Apr. 20, 2017

(51) Int. Cl.
*C07F 17/00*    (2006.01)
*C08F 4/6592*    (2006.01)
*C08F 10/02*    (2006.01)
*C07F 7/08*    (2006.01)
*C08F 4/659*    (2006.01)

(52) U.S. Cl.
CPC .............. *C08F 10/02* (2013.01); *C07F 7/082* (2013.01); *C07F 17/00* (2013.01); *C08F 4/65908* (2013.01); *C08F 4/65912* (2013.01); *C08F 4/65927* (2013.01)

(58) Field of Classification Search
CPC .............. C08F 4/65927; C08F 4/65908; C08F 4/65912; C08F 10/00
See application file for complete search history.

(56) References Cited

U.S. PATENT DOCUMENTS

| | | | |
|---|---|---|---|
| 5,064,802 A | 11/1991 | Stevens et al. | |
| 6,121,394 A | 9/2000 | Sugimoto et al. | |
| 6,683,150 B1 | 1/2004 | Meverden et al. | |
| 6,756,455 B2 | 6/2004 | Nagyl et al. | |
| 6,908,972 B2 | 6/2005 | Tsuie et al. | |
| 8,124,557 B2 | 2/2012 | Lee et al. | |
| 9,725,472 B2 * | 8/2017 | Lee .................. | C07F 7/082 |
| 2003/0148877 A1 | 8/2003 | Nifant'ev et al. | |
| 2003/0229188 A1 | 12/2003 | Nagy et al. | |
| 2006/0199726 A1 | 9/2006 | Nagy | |
| 2009/0062487 A1 | 3/2009 | Nagy et al. | |
| 2009/0062488 A1 | 3/2009 | Nagy et al. | |
| 2012/0123078 A1 | 5/2012 | Lee et al. | |
| 2013/0296497 A1 * | 11/2013 | Jeong ............... | C08F 297/08 525/321 |
| 2016/0159828 A1 | 6/2016 | Lee et al. | |
| 2016/0168281 A1 | 6/2016 | Lee et al. | |

FOREIGN PATENT DOCUMENTS

| | | |
|---|---|---|
| JP | 2001508083 A | 6/2001 |
| JP | 2008531838 A | 8/2008 |
| JP | 4540755 B2 | 9/2010 |
| KR | 1019940009020 B | 9/1994 |
| KR | 1020040085650 A | 10/2004 |
| KR | 1020050024287 A | 3/2005 |
| KR | 20110013286 A | 2/2011 |
| KR | 1020150037520 A | 4/2015 |
| KR | 1020150058938 A | 5/2015 |

* cited by examiner

*Primary Examiner* — Caixia Lu
(74) *Attorney, Agent, or Firm* — Dentons US LLP

(57) ABSTRACT

Provided are a novel metallocene compound, a catalyst composition including the same, and a method of preparing a polyolefin using the same. The metallocene compound according to the present invention and the catalyst composition including the same may be used for the preparation of a polyolefin, may have excellent polymerization ability, and may produce a polyolefin having an ultra-high molecular weight. In particular, when the metallocene compound according to the present invention is employed, an olefin-based polymer having an ultra-high molecular weight may be polymerized because the metallocene compound shows high polymerization activity even when it is supported on a support.

16 Claims, No Drawings

METALLOCENE COMPOUND, CATALYST COMPOSITION INCLUDING THE SAME, AND METHOD OF PREPARING POLYOLEFIN USING THE SAME

This application is a National Stage Application of International Application No. PCT/KR2015/000926, filed Jan. 28, 2015, the contents of which are incorporated herein by reference in their entirety for all purposes as if fully set forth below.

TECHNICAL FIELD

The present disclosure relates to a novel metallocene compound, a catalyst composition including the same, and a method of preparing a polyolefin using the same.

BACKGROUND OF THE INVENTION

In the early 1990s, [Me$_2$Si(Me$_4$C$_5$)NtBu]TiCl$_2$ (Constrained-Geometry Catalyst, hereinafter abbreviated as CGC) was reported by Dow Co. (U.S. Pat. No. 5,064,802), and superior aspects of the CGC in a copolymerization reaction of ethylene and alpha-olefin may be summarized by the following two points when compared to commonly known metallocene catalysts. (1) At a high polymerization temperature, high activity is shown and a polymer having a high molecular weight is produced, and (2) the copolymerization ability of alpha-olefin having large steric hindrance such as 1-hexene and 1-octene is excellent. In addition, a variety of characteristics of CGC upon polymerization are becoming gradually known, and thus thorough research into synthesis of derivatives thereof to serve as a polymerization catalyst is ongoing in academic and industrial fields.

A Group 4 transition metal compound having one or two cyclopentadienyl groups as a ligand may be used as a catalyst for olefin polymerization by activating it with methylaluminoxane or a boron compound. Such catalyst shows unique characteristics that a traditional Ziegler-Natta catalyst cannot realize.

That is, a polymer obtained by using such catalyst has a narrow molecular weight distribution and higher reactivity for a second monomer such as alpha-olefin or cycloolefin, and distribution of the second monomer in the polymer is even. Furthermore, it is possible to control the stereoselectivity of the polymer in the polymerization of alpha-olefin by changing the substituent of the cyclopentadienyl ligand in the metallocene catalyst, and it is easy to control the degree of copolymerization, the molecular weight, and the distribution of the second monomer upon copolymerization of ethylene and other olefins.

Meanwhile, since the metallocene catalyst is more expensive than the Ziegler-Natta catalyst, it must have good activity for its economic cost. If the metallocene catalyst has high reactivity for the second monomer, there is an advantage that a polymer including a large amount of the second monomer may be obtained by using only a small amount of the second monomer.

Many researchers have studied various catalysts, and as a result, it is proven that a bridged catalyst generally has high reactivity for the second monomer. The bridged catalysts developed until now may be classified into three types according the type of the bridge. One is a catalyst of which two cyclopentadienyl ligands are connected with an alkylene dibridge by the reaction of an electrophile such as an alkyl halide and indene or fluorene, another is a silicone-bridged catalyst of which the ligands are connected with —SiR$_2$—, and the other is a methylene-bridged catalyst which is obtained by the reaction of fulvene and indene or fluorene.

Among the above attempts, however, very few catalysts have been practically applied in commercial factories, and thus preparation of catalysts showing more improved polymerization performance is still required.

OBJECTIVES OF THE INVENTION

In order to solve the problems of the prior art, the present invention provides a metallocene compound having excellent activity and that is capable of producing a polyolefin having a high molecular weight, a catalyst composition including the same, a method of preparing a polyolefin using the same, and a polyolefin prepared by using the same.

Particularly, the present invention provides a metallocene compound which shows high polymerization activity even when it is supported on a support and is able to polymerize an olefin-based polymer having an ultra-high molecular weight, a catalyst composition including the same, a method of preparing an olefin-based polymer using the same, and an olefin-based polymer prepared by using the same.

Means for Achieving the Objectives

The present invention provides a metallocene compound represented by the following Chemical Formula 1:

[Chemical Formula 1]

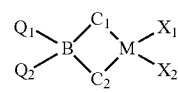

wherein Q$_1$ and Q$_2$ are the same as or different from each other, and are each independently hydrogen, a halogen, a C1 to C20 alkyl group, a C2 to C20 alkenyl group, a C2 to C20 alkoxyalkyl group, a C6 to C20 aryl group, a C7 to C20 alkylaryl group, or a C7 to C20 arylalkyl group;

B is carbon, silicon, or germanium;

M is a Group 4 transition metal;

X$_1$ and X$_2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and one of C$_1$ and C$_2$ is represented by the following Chemical Formula 2a or Chemical Formula 2b, and the other of C$_1$ and C$_2$ is represented by the following Chemical Formula 3a, Chemical Formula 3b, or Chemical Formula 3c,

[Chemical Formula 2a]

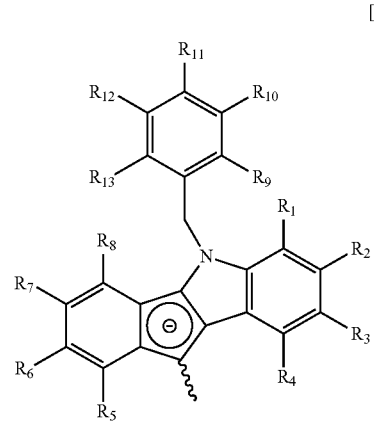

[Chemical Formula 2b]

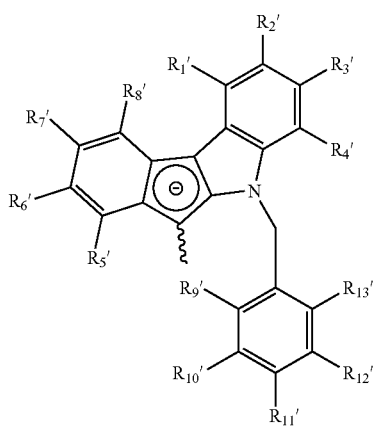

[Chemical Formula 3a]

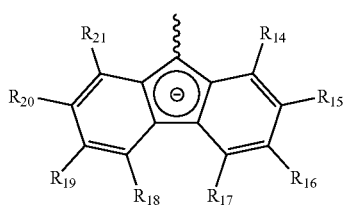

[Chemical Formula 3b]

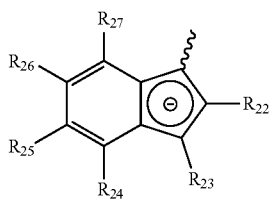

[Chemical Formula 3c]

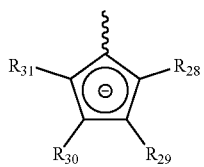

in Chemical Formulae 2a, 2b, 3a, 3b, and 3c, R1 to R31 and R1' to R13' are the same as or different from each other, and are each independently hydrogen, a halogen, a C1 to C20 alkyl group, a C1 to C20 haloalkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, provided that one or more of R9 to R13 and R9' to R13' are a C1 to C20 haloalkyl group, two or more neighboring groups of R14 to R31 are connected to each other to form a substituted or unsubstituted aliphatic or aromatic ring, and B and M of Chemical Formula 1 are bonded to the cyclopentadienyl groups of $C_1$ and $C_2$ of Chemical Formula 1.

Further, the present invention provides a catalyst composition including the metallocene compound.

The present invention also provides a method of preparing a polyolefin, including the step of polymerizing olefin-based monomers in the presence of the catalyst composition.

In addition, the present invention provides a polyolefin prepared by the preparation method.

Effects of the Invention

A metallocene compound according to the present invention or a catalyst composition including the same may be used for the preparation of a polyolefin, may have excellent activity, and may produce a polyolefin having a high molecular weight.

In particular, when the metallocene compound according to the present invention is employed, a polyolefin having an ultra-high molecular weight may be polymerized because the metallocene compound shows high polymerization activity even when it is supported on a support.

Furthermore, the activity of the catalyst may be maintained for a long residence time in a reactor because of its long lifetime.

DETAILED DESCRIPTION OF THE EMBODIMENT

In the present invention, the terms "the first", "the second", and the like are used to describe a variety of components, and these terms are merely employed to differentiate a certain component from other components.

Further, the terms used in this description are just for explaining exemplary embodiments, and are not intended to restrict the present invention. The singular expression may include the plural expression unless it is differently expressed contextually. It must be understood that the term "include", "equip", or "have" in the present description is only used for designating the existence of characteristics taking effect, numbers, steps, components, or combinations thereof, and do not exclude the existence or the possibility of addition of one or more different characteristics, numbers, steps, components of combinations thereof beforehand.

The present invention may be variously modified and have various forms, and specific examples of the present invention are explained in this description. However, it is not intended to limit the present invention to the specific examples, and it must be understood that the present invention includes all modifications, equivalents, or replacements included in the spirit and technical scope of the present invention.

Hereinafter, the present invention will be described in more detail.

A metallocene compound according to the present invention is characterized in that it is represented by the following Chemical Formula 1:

[Chemical Formula 1]

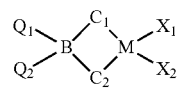

wherein $Q_1$ and $Q_2$ are the same as or different from each other, and are each independently hydrogen, a halogen, a C1 to C20 alkyl group, a C2 to C20 alkenyl group, a C2 to C20 alkoxyalkyl group, a C6 to C20 aryl group, a C7 to C20 alkylaryl group, or a C7 to C20 arylalkyl group;

B is carbon, silicon, or germanium;

M is a Group 4 transition metal;

$X_1$ and $X_2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and one of $C_1$ and $C_2$ is represented by the following Chemical Formula 2a or Chemical Formula 2b, and the other of $C_1$ and $C_2$ is represented by the following Chemical Formula 3a, Chemical Formula 3b, or Chemical Formula 3c,

[Chemical Formula 2a]

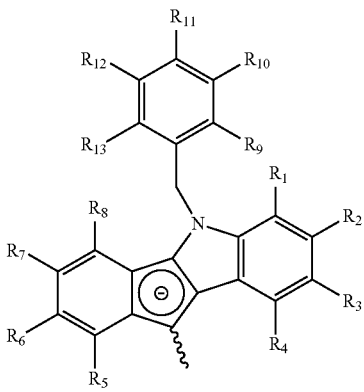

[Chemical Formula 2b]

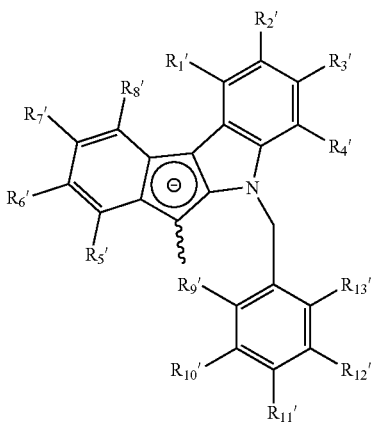

[Chemical Formula 3a]

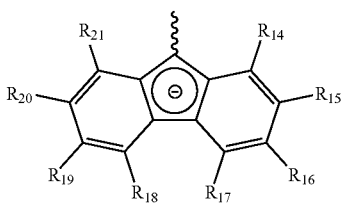

[Chemical Formula 3b]

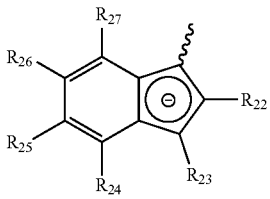

[Chemical Formula 3c]

wherein in Chemical Formulae 2a, 2b, 3a, 3b and 3c, $R_1$ to $R_{31}$ and $R_{1'}$ to $R_{13'}$ are the same as or different from each other, and are each independently hydrogen, a halogen, a C1 to C20 alkyl group, a C1 to C20 haloalkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, provided that one or more of $R_9$ to $R_{13}$ and $R_{9'}$ to $R_{13'}$ are a C1 to C20 haloalkyl group, two or more neighboring groups of $R_{14}$ to $R_{31}$ are connected to each other to form a substituted or unsubstituted aliphatic or aromatic ring, and B and M of Chemical Formula 1 are bonded to the cyclopentadienyl groups of $C_1$ and $C_2$ of Chemical Formula 1.

In the present invention, Chemical Formula 2a or Chemical Formula 2b is used in any one of $C_1$ and $C_2$ in Chemical Formula 1, and a cyclopentadiene-based substituent group with lower steric hindrance may be used in the other of $C_1$ and $C_2$, thereby producing a polyolefin having a high molecular weight and maintaining excellent copolymerization ability and hydrogen reactivity.

In the metallocene compound according to the present invention, the substituents of Chemical Formula 1 are more specifically explained as follows.

The C1 to C20 alkyl group may include a linear or branched alkyl group, and specifically, it may be a methyl group, an ethyl group, a propyl group, an isopropyl group, an n-butyl group, a tert-butyl group, a pentyl group, a hexyl group, a heptyl group, an octyl group, or the like, but is not limited thereto.

The C2 to C20 alkenyl group may include a linear or branched alkenyl group, and specifically, it may be an allyl group, an ethenyl group, a propenyl group, a butenyl group, a pentenyl group, or the like, but is not limited thereto.

The C6 to C20 aryl group may include a single ring aryl group or a condensed ring aryl group, and specifically, it may be a phenyl group, a biphenyl group, a naphthyl group, a phenanthrenyl group, a fluorenyl group, or the like, but is not limited thereto.

The C5 to C20 heteroaryl group may include a single ring heteroaryl group or a condensed ring heteroaryl group, and specifically, it may be a carbazolyl group, a pyridyl group, a quinoline group, an isoquinoline group, a thiophenyl group, a furanyl group, an imidazole group, an oxazolyl group, a thiazolyl group, a triazine group, a tetrahydropyranyl group, a tetrahydrofuranyl group, or the like, but is not limited thereto.

The C1 to C20 alkoxy group may be a methoxy group, an ethoxy group, a phenyloxy group, a cyclohexyloxy group, or the like, but is not limited thereto.

The C2 to C20 alkoxyalkyl group may be prepared by substituting one or more hydrogens of the above described C1 to C20 alkyl group with the above described alkoxy group, and for example, it may be a tert-butoxyhexyl group, or the like, but is not limited thereto.

The C1 to C20 haloalkyl group may be prepared by substituting one or more hydrogens of the above described C1 to C20 alkyl group with a halogen, and for example, it may be a fluoroalkyl group, namely, $CF_3$, $CF_3CH_2$, $CF_3CF_2$, $CFH_2$ or the like, but is not limited thereto.

The Group 4 transition metal may be titanium, zirconium, hafnium, or the like, but is not limited thereto.

In the metallocene compound according to the present invention, it is more preferable that $R_1$ to $R_{31}$ and $R_{1'}$ to $R_{13'}$ in Chemical Formulae 2a, 2b, 3a, 3b, and 3c are each independently hydrogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, an ethoxy group, a fluoroalkyl group, or the like, but is not limited thereto.

In the metallocene compound according to the present invention, it is preferable that $Q_1$ and $Q_2$ in Chemical Formula 1 are each independently hydrogen, a methyl group, an ethyl group, a propyl group, an isopropyl group, an n-butyl group, a tert-butyl group, a methoxymethyl group, a tert-butoxymethyl group, a tert-butoxyhexyl group, a 1-ethoxyethyl group, a 1-methyl-1-methoxyethyl group, a tetrahydropyranyl group, or a tetrahydrofuranyl group, but is not limited thereto.

In the metallocene compound according to the present invention, B in Chemical Formula 1 is preferably silicon, but is not limited thereto.

Since the metallocene compound of Chemical Formula 1 includes a structure in which an indenoindole derivative and a cyclopentadiene derivative are asymmetrically crosslinked by a bridge, and has an unshared electron pair acting as a Lewis base in the ligand structure, the metallocene compound may show high polymerization activity even when it is supported on the surface of a support having a Lewis acid characteristic. Further, the metallocene compound has high activity because of including the electron-rich indenoindole group and the cyclopentadiene group, and maintains excellent copolymerization ability and high activity because of proper steric hindrance and an electronic effect of the ligand. Furthermore, the metallocene compound may be used to prepare a polyolefin having an ultra high molecular weight because a nitrogen atom of the indenoindole derivative stabilizes the beta-hydrogen of a growing polymer chain by hydrogen bonding and inhibits beta-hydrogen elimination. In particular, one or more of $R_9$ to $R_{13}$ and $R_{9'}$ to $R_{13'}$ in the metallocene compound of Chemical Formula 1 may include a C1 to C20 haloalkyl group, for example, a fluoroalkyl group, namely $CF_3$ or the like, which acts like the nitrogen atom of the indenoindole derivative to stabilize the beta-hydrogen of the growing polymer chain by hydrogen bonding, to further inhibit beta-hydrogen elimination, and to achieve more effective polymerization of a polyolefin having an ultra-high molecular weight. In other words, a substituent such as a stronger hydrogen bond acceptor, $CF_3$ etc., is introduced while maintaining the basic skeleton of the catalyst, in which the indenoindole derivative and the cyclopentadiene derivative are asymmetrically crosslinked by a bridge, so as to stabilize the beta-hydrogen by hydrogen bonding and to increase the effect of inhibiting beta-hydrogen elimination, thereby polymerizing a polyolefin having an ultra-high molecular weight.

According to an embodiment of the present invention, a specific example of the compound represented by Chemical Formula 2a may be a compound represented by the following structural formula, but is not limited thereto.

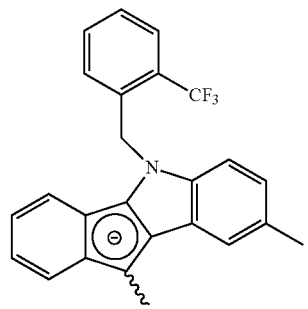

According to an embodiment of the present invention, a specific example of the compound represented by Chemical Formula 2b may be a compound represented by the following structural formula, but is not limited thereto.

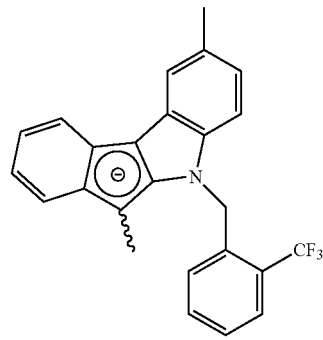

According to an embodiment of the present invention, a specific example of the compound represented by Chemical Formula 3a may be a compound represented by any one of the following structural formulae, but is not limited thereto.

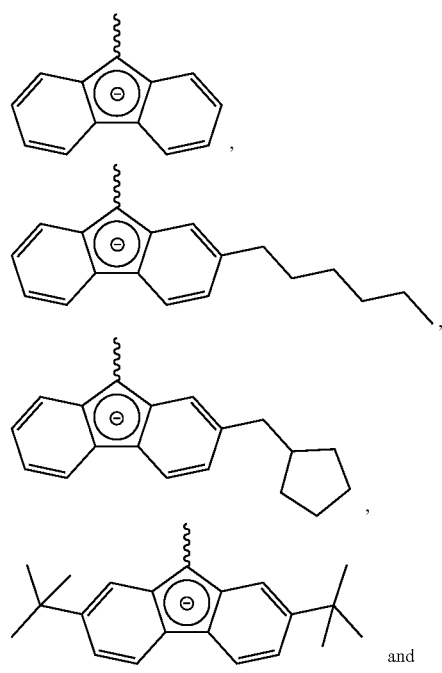

and

-continued

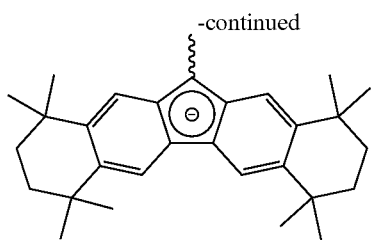

According to an embodiment of the present invention, a specific example of the compound represented by Chemical Formula 3b may be a compound represented by the following structural formula, but is not limited thereto.

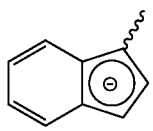

According to an embodiment of the present invention, a specific example of the compound represented by Chemical Formula 3c may be a compound represented by the following structural formula, but is not limited thereto.

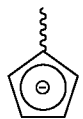

According to an embodiment of the present invention, a specific example of the compound represented by Chemical Formula 1 may be a compound represented by the following structural formula, but is not limited thereto.

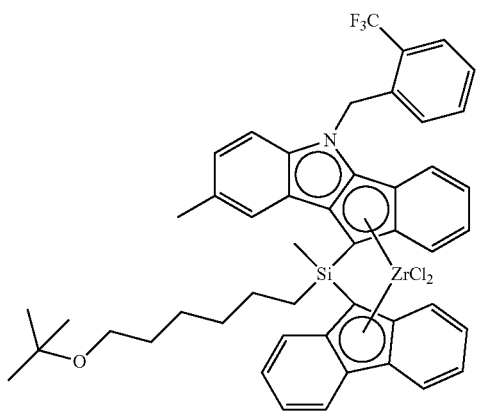

The metallocene compound according to the present invention may have excellent activity and may polymerize a polyolefin having a high molecular weight. In particular, the metallocene compound may exhibit high polymerization activity when it is used in a non-supported form without using a separate support and also used in the form of being supported on a support. In particular, the metallocene compound may be used to prepare an ultra-high-molecular-weight polyolefin having a high average molecular weight even in the absence of hydrogen.

Furthermore, the metallocene compound according to the present invention may polymerize a polyolefin having an ultra-high molecular weight while still having high activity, even when the polymerization reaction is carried out in the presence of hydrogen in order to prepare a polyolefin having a high molecular weight and a wide molecular weight distribution at the same time. Therefore, the metallocene compound may prepare a polyolefin satisfying the high molecular characteristic without a decrease in activity even when the metallocene compound is heterogeneously used together with a catalyst having different characteristics, and thus the olefin-based polymer having a high molecular weight and a wide molecular weight distribution may be easily prepared.

According to an embodiment of the present invention, the metallocene compound of Chemical Formula 1 may be obtained by connecting an indenoindole derivative (C1) and a cyclopentadiene derivative (C2) with a bridge compound to prepare a ligand compound, and carrying out metallation by adding a metal precursor compound, but is not limited thereto.

More specifically, for example, after preparing a lithium salt by reacting the indenoindole derivative (C1) and the cyclopentadiene derivative (C2) with an organic lithium compound such as n-BuLi, a halogenated compound of a bridge compound may be mixed therewith and then this mixture may be reacted to prepare the ligand compound. After mixing the ligand compound or the lithium salt thereof and the metal precursor compound, and reacting them for about 12 to 24 h until the reaction is completed, the reaction mixture may be filtered and dried under reduced pressure to obtain the metallocene compound represented by Chemical Formula 1.

A preparation method of the metallocene compound of the present invention is concretely explained in the following examples.

The present invention also provides a catalyst composition including the metallocene compound and a cocatalyst.

The catalyst composition according to the present invention may further include one or more of cocatalyst compounds represented by the following Chemical Formula 4, Chemical Formula 5, and Chemical Formula 6, in addition to the metallocene compound:

—[Al(R$_{32}$)—O]$_n$—      [Chemical Formula 4]

wherein, in Chemical Formula 4,

R$_{32}$'s may be the same as or different from each other, and are each independently a halogen; a hydrocarbon having 1 to 20 carbon atoms; or a halogen-substituted hydrocarbon having 1 to 20 carbon atoms; and n is an integer of 2 or more;

J(R$_{32}$)$_3$      [Chemical Formula 5]

wherein, in Chemical Formula 5,

R$_{32}$ may be the same as defined in Chemical Formula 4; and

J is aluminum or boron;

[E-H]$^+$[ZA'$_4$]$^-$ or [E]$^+$[ZA'$_4$]$^-$      [Chemical Formula 6]

wherein, in Chemical Formula 6,

E is a neutral or cationic Lewis acid;

H is a hydrogen atom;

Z is a Group 13 element; and

A's may be the same as or different from each other, and are each independently an aryl group having 6 to 20 carbon atoms or an alkyl group having 1 to 20 carbon atoms, of which one or more hydrogen atoms are unsubstituted or substituted with a halogen, a hydrocarbon having 1 to 20 carbon atoms, alkoxy, or phenoxy.

Examples of the compound represented by Chemical Formula 4 may include methylaluminoxane, ethylaluminoxane, isobutylaluminoxane, butylaluminoxane, or the like, and a more preferred compound may be methylaluminoxane.

Examples of the compound represented by Chemical Formula 5 may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, or the like, and a more preferred compound may be selected from trimethylaluminum, triethylaluminum, and triisobutylaluminum.

Examples of the compound represented by Chemical Formula 6 may include triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl)aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylaniliniurn tetrapentafluorophenylaluminum, diethylammonium tetrapentatetraphenylaluminum, triphenylphosphonium tetraphenylaluminum, trimethylphosphonium tetraphenylaluminum, tripropylammonium tetra(p-tolyl)boron, triethylammonium tetra(o,p-dimethylphenyl)boron, tributylammonium tetra(p-trifluoromethylphenyl)boron, triphenylcarbonium tetra(p-trifluoromethylphenyl)boron, triphenylcarbonium tetrapentafluorophenylboron, or the like.

Alumoxane may be preferably used, and an alkyl alumoxane, methylalumoxane (MAO), may be more preferably used.

The catalyst composition according to the present invention may be prepared by a first method including the steps of 1) contacting the metallocene compound represented by Chemical Formula 1 with the compound represented by Chemical Formula 4 or Chemical Formula 5 to obtain a mixture; and 2) adding the compound represented by Chemical Formula 6 to the mixture.

Further, the catalyst composition according to the present invention may be prepared by a second method of contacting the metallocene compound represented by Chemical Formula 1 with the compound represented by Chemical Formula 4.

In the first method of preparing the catalyst composition, a molar ratio of the metallocene compound represented by Chemical Formula 1/the compound represented by Chemical Formula 4 or Chemical Formula 5 is preferably 1/5,000 to 1/2, more preferably 1/1,000 to 1/10, and most preferably 1/500 to 1/20. When the molar ratio of the metallocene compound represented by Chemical Formula 1/the compound represented by Chemical Formula 4 or Chemical Formula 5 exceeds 1/2, there is a problem that an amount of the alkylating agent is very small and the metal compound is not completely alkylated, and when the molar ratio is less than 1/5,000, the alkylation of the metal compound is accomplished, but there is a problem that the alkylated metal compound is not completely activated due to the side reaction between the remaining excess alkylating agent and the activator of Chemical Formula 6. Furthermore, the molar ratio of the metallocene compound represented by Chemical Formula 1/the compound represented by Chemical Formula 6 is preferably 1/25 to 1, more preferably 1/10 to 1, and most preferably 1/5 to 1. When the molar ratio of the metallocene compound represented by Chemical Formula 1/the compound represented by Chemical Formula 6 exceeds 1, there is a problem that the activity of the prepared catalyst composition is deteriorated because the amount of the activator is relatively small and the metal compound is not completely activated, and when the molar ratio is less than 1/25, the activation of the metal compound is completely accomplished, but there is a problem that the cost of the catalyst composition is not economical or the purity of the polymer to be prepared is decreased due to the remaining excess activator.

In the second method of preparing the catalyst composition, the molar ratio of the metallocene compound represented by Chemical Formula 1/the compound represented by Chemical Formula 4 is preferably 1/10,000 to 1/10, more preferably 1/5,000 to 1/100, and most preferably 1/3,000 to 1/500. When the molar ratio exceeds 1/10, there is a problem that the activity of the prepared catalyst composition is deteriorated because the amount of the activator is relatively small and the metal compound is not completely activated, and when the molar ratio is less than 1/10,000, the activation of the metal compound is completely accomplished, but there is a problem that the cost of the catalyst composition is not economical or the purity of the polymer to be prepared is decreased due to the remaining excess activator.

As a reaction solvent used upon preparation of the catalyst composition, a hydrocarbon solvent such as pentane, hexane, heptane, etc., or an aromatic solvent such as benzene, toluene, etc., may be used.

Furthermore, the catalyst composition may include the metallocene compound and the cocatalyst compound in the form of being supported on a support.

When the metallocene compound and the cocatalyst compound are used in the form of being supported on the support, the metallocene compound may be included in an amount of about 0.5 to about 20 parts by weight and the cocatalyst may be included in an amount of about 1 to about 1,000 parts by weight, based on 100 parts by weight of the support. Preferably, the metallocene compound may be included in an amount of about 1 to about 15 parts by weight and the cocatalyst may be included in an amount of about 10 to about 500 parts by weight, based on 100 parts by weight of the support. Most preferably, the metallocene compound may be included in an amount of about 1 to about 100 parts by weight and the cocatalyst may be included in an amount of about 40 to about 150 parts by weight, based on 100 parts by weight of the support.

Meanwhile, as long as the support is a metal, a metal salt, or a metal oxide which is commonly used in a supported catalyst, there is no limitation in the constitution. Specifically, the support may include any one support selected from the group consisting of silica, silica-alumina, and silica-magnesia. The support may be dried at as high temperature, and generally it may include an oxide, a carbonate, a sulfate, or a nitrate of a metal, such as $Na_2O$, $K_2CO_3$, $BaSO_4$, $Mg(NO_3)_2$, etc.

It is better that the amount of hydroxy (—OH) groups on the surface of the support is as small as possible, but it is practically difficult to eliminate all of hydroxy groups. The amount of hydroxy groups may be controlled by the preparation method, the preparation conditions, the drying conditions (temperature, time, drying method, etc.) of the support, and the amount of hydroxy groups is preferably 0.1 mmol/g to 10 mmol/g, more preferably 0.1 mmol/g to 1 mmol/g, and more preferably 0.1 mmol/g to 0.5 mmol/g. In order to reduce the side-reaction by some hydroxy groups left after drying, a support, from which hydroxy groups are chemically eliminated while preserving highly reactive siloxane groups participating in supporting, may be used.

Further, the present invention provides a method of preparing a polyolefin, including the step of polymerizing olefin-based monomers in the presence of the catalyst composition including the metallocene compound, and a polyolefin prepared by the preparation method.

The polymerization reaction may be carried out according to a solution polymerization process, a slurry process, or a gas phase process by using a continuous slurry polymerization reactor, a loop slurry reactor, a gas phase reactor, or a solution reactor. Furthermore, the reaction may be homopolymerization of an olefin-based monomer or copolymerization of two or more monomers.

The polymerization of the olefin-based monomer may be carried out at a temperature of about 25° C. to about 500° C. and at a pressure of about 1 kgf/cm² to about 100 kgf/cm² for about 1 h to about 24 h. Specifically, the polymerization of the olefin-based monomer may be carried out at a temperature of about 25° C. to about 500° C., preferably about 25° C. to about 200° C., and more preferably about 50° C. to about 100° C. Furthermore, the reaction pressure may be about 1 kgf/cm² to about 100 kgf/cm², preferably about 1 kgf/cm² to about 50 kgf/cm², and more preferably about 5 kgf/cm² to about 40 kgf/cm².

Further, when the solution polymerization process is applied to the preparation of olefin-based monomers by using the metallocene compound of the present invention, a paraffin-based solvent and an aromatic solvent may be used. The solution polymerization process may be carried out, for example, in the presence of one or more solvents selected from the group consisting of benzene, toluene, xylene, isobutane, pentane, hexane, and heptane.

In the polyolefin prepared according to the present invention, specific examples of the olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, or the like, and the olefin-based monomer may be a copolymer prepared by copolymerizing two or more of the monomers.

The polyolefin may be a polyethylene polymer, but is not limited thereto.

If the polyolefin is a copolymer of ethylene/alpha-olefin, the content of a comonomer, alpha-olefin, is not particularly limited, and it may be adequately selected according to the use or purpose of the polyolefin. More specifically, the content may be more than 0 mol % and 99 mol % or less.

The polyolefin to be prepared may exhibit a high molecular weight.

According to an embodiment of the present invention, a weight average molecular weight (Mw) of the polyolefin may be about 50,000 g/mol to about 5,000,000 g/mol, or about 70,000 g/mol to about 4,500,000 g/mol. In particular, when the polyolefin is prepared by using the catalyst composition which is prepared by supporting the metallocene compound on a support, it is possible to prepare a polyolefin having a high molecular weight of about 500,000 g/mol or more, for example, about 500,000 g/mol to about 5,000,000 g/mol, or about 500,000 g/mol to about 4,500,000 g/mol.

Furthermore, a molecular weight distribution (Mw/Mn) of the polyolefin may be about 1.5 to about 20, and preferably about 2.0 to about 10.

In addition, according to an embodiment of the present invention, the density of the polyolefin may be about 0.85 g/cm³ to about 0.96 g/cm³, and preferably about 0.90 g/cm³ to about 0.95 g/cm³.

Therefore, the polyolefin according to the present invention shows an ultra-high molecular weight, thereby being applied to a variety of fields according to its use.

Hereinafter, the preferred examples are provided for better understanding. However, these examples are for illustrative purposes only, and the invention is not intended to be limited by these examples.

EXAMPLES

Preparation Example of Metallocene Compound

Example 1

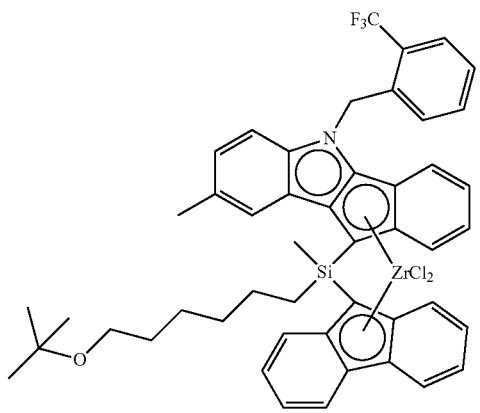

1-1 Preparation of Ligand Compound

After dissolving 2.9 g (7.4 mmol) of 8-methyl-5-(2-(trifluoromethyl)benzyl)-5,10-dihydroindeno[1,2-b]indole in 100 mL of hexane and 2 mL (16.8 mmol) of MTBE (methyl tertiary butyl ether), 3.2 mL (8.1 mmol) of a 2.5 M n-BuLi hexane solution was added thereto dropwise in a dry ice/acetone bath and the mixture was agitated overnight at room temperature. In another 250 mL Schlenk flask, 2 g (7.4 mmol) of (6-tert-butoxyhexyl)dichloro(methyl)silane was dissolved in 50 mL of hexane, and then added dropwise in a dry ice/acetone bath. A lithiated slurry of 8-methyl-5-(2-(trifluoromethyl)benzyl)-5,10-dihydroindeno[1,2-b]indole was added dropwise via a cannula. After complete addition, the temperature of the mixture was slowly raised to room temperature, followed by agitation overnight. At the same time, 1.2 g (7.4 mmol) of fluorene was dissolved in 100 mL of THF, and 3.2 mL (8.1 mmol) of a 2.5 M n-BuLi hexane solution was added dropwise in a dry ice/acetone bath, followed by agitation at room temperature overnight.

Completion of the reaction was confirmed by NMR sampling of a reaction solution (Si solution) of 8-methyl-5-(2-(trifluoromethyl)benzyl)-5,10-dihydroindeno[1,2-b]indole and (6-(tert-butoxy)hexyl)dichloro(methyl)silane.

$^1$H NMR (500 MHz, CDCl$_3$): 7.74-6.49 (11H, m), 5.87 (2H, s), 4.05 (1H, d), 3.32 (2H, m), 3.49 (3H, s), 1.50-1.25 (8H, m), 1.15 (9H, s), 0.50 (2H, m), 0.17 (3H, d)

After confirming the previous synthesis, a lithiated solution of fluorene was slowly added dropwise to the Si solution in a dry ice/acetone bath, followed by agitation at room temperature overnight. After reaction, extraction was performed with ether/water, residual water was removed from an organic layer with MgSO$_4$, and the solvent was removed under reduced pressure to obtain 5.5 g (7.4 mmol) of a ligand compound in an oil phase, which was identified by $^1$H NMR.

$^1$H NMR (500 MHz, CDCl$_3$): 7.89-6.53 (19H, m), 5.82 (2H, s), 4.26 (1H, d), 4.14-4.10 (1H, m), 3.19 (3H, s), 2.40 (3H, m), 1.35-1.21 (6H, m), 1.14 (9H, s), 0.97-0.9 (4H, m), −0.34 (3H, t).

1-2 Preparation of Metallocene Compound

After dissolving 5.4 g (Mw 742.00, 7.4 mmol) of the ligand compound synthesized in 1-1 in 80 mL of toluene and 3 mL (25.2 mmol) of MTBE, 7.1 mL (17.8 mmol) of a 2.5 M n-BuLi hexane solution was added thereto dropwise in a dry ice/acetone bath, followed by agitation at room temperature overnight. 3.0 g (8.0 mmol) of ZrCl$_4$(THF)$_2$ was added to 80 mL of toluene to prepare a slurry. 80 mL of ZrCl$_4$(THF)$_2$/toluene slurry was transferred to the ligand-Li solution in a dry ice/acetone bath, followed by agitation at room temperature overnight.

The reaction solution was filtered to eliminate LiCl. After vacuum-drying the filtrate to eliminate toluene therefrom, 100 mL of hexane was added thereto, followed by sonication for 1 h. After filtration, 3.5 g (yield of 52 mol %) of a filtered solid, a violet-colored metallocene compound, was obtained.

$^1$H NMR (500 MHz, CDCl$_3$): 7.90-6.69 (9H, m), 5.67 (2H, s), 3.37 (2H, m), 2.56 (3H,$), 2.13-1.51 (11H, m), 1.17 (9H, s).

Preparation Examples of Supported Catalysts

Catalyst Preparation Example 1

A silica support was prepared by dehydrating silica (SY-LOPOL 948, produced by Grace Davison Co.) at 400° C. under vacuum for 12 h.

After adding 100 mL of a toluene solution in a glass reactor at room temperature and adding 10 g of the prepared silica support (SP2410), the solution was agitated while elevating the temperature of the reactor to 40° C. When the silica was sufficiently dispersed, 60.6 mL of a 10 wt % methylaluminoxane (MAO)/toluene solution was added thereto and the mixture was agitated at 500 rpm for 16 h after elevating the temperature to 60° C. Subsequently, the temperature was decreased to 40° C., and the unreacted aluminum compound was eliminated by washing with a sufficient amount of toluene. After adding 100 mL of toluene therein, 0.1 mmol of the metallocene compound prepared in Preparation Example 1 was added thereto and the mixture was agitated for 2 h. After stopping agitation when the reaction was completed, a toluene layer was separated and eliminated therefrom, and 100 mL of toluene and 4.5 mL of a 2 wt % ASA/hexane solution were added, followed by agitation at 500 rpm for 10 min. After stopping agitation when the reaction was completed, a toluene layer was separated and eliminated therefrom, and 100 mL of hexane was added, followed by agitation for 10 min. After stopping agitation, a hexane slurry was transferred to a flask, and then a supported catalyst was obtained by eliminating the remaining solvent under reduced pressure.

Examples of Polyethylene Polymerization

Polymerization Preparation Example 1

Polymerization of Ethylene

A 300 mL Andrew bottle was prepared and assembled with an impeller part, and then air in the bottle was replaced by argon in a glove box. After adding 70 mL of toluene to the Andrew bottle, 10 mL of an MAO (10 wt % in toluene) solution was added thereto. 20 µmol of the metallocene compound catalyst prepared in Preparation Example 1 was added to a separate 100 mL flask, and dissolved in 20 mL of toluene. 5 mL (5 µmol) of the catalyst solution was taken and injected into the Andrew bottle, followed by agitation for 5 min. The Andrew bottle was immersed in an oil bath heated to 90° C. and a mechanical stirrer was fixed at the upper part of the bottle. The air in the bottle was purged with ethylene gas 3 times, and pressure was slowly raised up to 50 psig by opening an ethylene valve. The reaction was allowed to continue for 30 min while operating the mechanical stirrer at 500 rpm while maintaining the pressure by continuously providing ethylene of as much as was consumed. When the reaction was completed, the gas in the reactor was slowly vented after locking the ethylene valve and stopping agitation. After disassembling the cover of the reactor, the reactant was poured in 400 mL of an ethanol/HCl aqueous solution mixture, and the mixture was agitated for about 2 h. The polymer obtained by filtration was dried at 65° C. for 20 h in a vacuum oven. The obtained polymer was weighed to calculate the activity of the catalyst, and used for additional analysis.

MAO premix polymerization was performed by using 5 mL (2.5 µmol) of a catalyst solution which was prepared by adding 10 µmol of the metallocene compound catalyst of Preparation Example 1 in a separate 100 mL-flask and dissolving the metallocene compound catalyst in 20 mL of MAO (10 wt % in toluene).

Polymerization Preparation Example 2

Copolymerization of Ethylene-1-Hexene

A 300 mL Andrew bottle was prepared and assembled with an impeller part, and then air in the bottle was replaced by argon in a glove box. After adding 70 mL of toluene to the Andrew bottle, 10 mL of an MAO (10 wt % in toluene) solution was added thereto. 20 µmol of the metallocene compound catalyst prepared in Preparation Example 1 was added to a separate 100 mL flask, and dissolved in 20 mL of toluene. 5 mL (5 µmol) of the catalyst solution was taken and injected into the Andrew bottle, followed by agitation for 5 min. The Andrew bottle was immersed in an oil bath heated to 90° C. and a mechanical stirrer was fixed at the upper part of the bottle. 5 mL of 1-hexene was injected under an argon atmosphere, the air in the bottle was purged with ethylene gas 3 times, and pressure was slowly raised up to 50 psig by opening an ethylene valve. The reaction was allowed to continue for 30 min while operating the mechanical stirrer at 500 rpm and while maintaining the pressure by continuously providing ethylene of as much as was consumed. When the reaction was completed, the gas in the reactor was slowly vented after locking the ethylene valve and stopping agitation. After disassembling the cover of the reactor, the reactant was poured in 400 mL of an ethanol/HCl aqueous solution mixture, and the mixture was agitated for 1 h. The polymer obtained by filtration was dried at 65° C. for 20 h in a vacuum oven. The obtained polymer was weighed to calculate the activity of the catalyst, and used for additional analysis.

MAO premix polymerization was performed by using 5 mL (2.5 µmol) of a catalyst solution which was prepared by adding 10 µmol of the metallocene compound catalyst of Preparation Example 1 in a separate 100 mL-flask and dissolving the metallocene compound catalyst in 20 mL of MAO (10 wt % in toluene).

Polymerization Preparation Example 3

A polymerization process was carried out in the same manner as in Polymerization Preparation Example 1, except that 20 µmol of the metallocene compound catalyst of Preparation Example 1 was added, and dissolved in 20 mL of toluene, and then 2.5 mL (2.5 µmol) of the catalyst solution was taken and injected.

Polymerization Preparation Example 4

A polymerization process was carried out in the same manner as in Polymerization Preparation Example 1, except that 20 µmol of the metallocene compound catalyst of Preparation Example 1 was added, and dissolved in 20 mL of toluene, and then 2.5 mL (2.5 µmol) of the catalyst solution was taken and injected.

The polymerization process conditions, activities of the catalysts, and analysis results of the obtained polymers in Polymerization Preparation Examples 1 to 4 are given in the following Table 1.

TABLE 1

| | Type of catalyst | Cat. (µmol) | 1-Hexene (mL) | Time (min) | Activity (kg/mol Cat/h, $10^6$) | Mw | PDI | 1-Hexene content (mol %) |
|---|---|---|---|---|---|---|---|---|
| Polymerization Preparation Example 1 | Example 1 | 5 | — | 10 | 7.2 | 433,077 | 2.27 | — |
| Polymerization Preparation Example 2 | Example 1 | 5 | 5 | 15 | 5.44 | 311,454 | 2.14 | 5.4 |
| Polymerization Preparation Example 3 | Example 1 | 2.5 | — | 10 | 11.2 | 403,000 | 2.7 | — |
| Polymerization Preparation Example 4 | Example 1 | 2.5 | 5 | 12 | 14.2 | 259,000 | 2.7 | 7.1 |

The invention claimed is:

1. A metallocene compound represented by the following Chemical Formula 1:

[Chemical Formula 1]

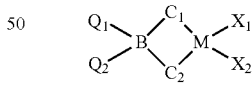

wherein $Q_1$ and $Q_2$ are the same as or different from each other, and are each independently hydrogen, a halogen, a C1 to C20 alkyl group, a C2 to C20 alkenyl group, a C2 to C20 alkoxyalkyl group, a C6 to C20 aryl group, a C7 to C20 alkylaryl group, or a C7 to C20 arylalkyl group;

B is carbon, silicon, or germanium;

M is a Group 4 transition metal;

$X_1$ and $X_2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and one of $C_1$ and $C_2$ is represented by the following Chemical Formula 2a or Chemical Formula 2b, and the other of $C_1$ and $C_2$ is represented by the following Chemical Formula 3a, Chemical Formula 3b, or Chemical Formula 3c,

[Chemical Formula 2a]

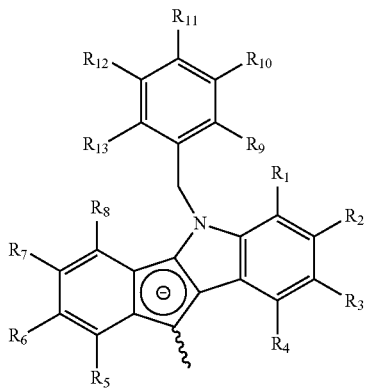

[Chemical Formula 2b]

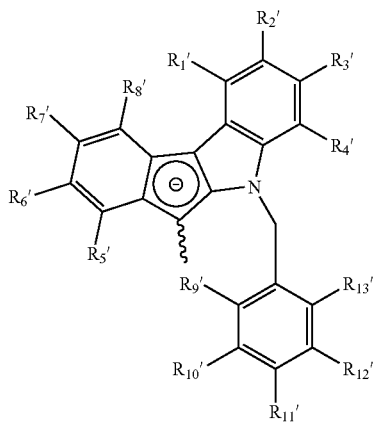

[Chemical Formula 3a]

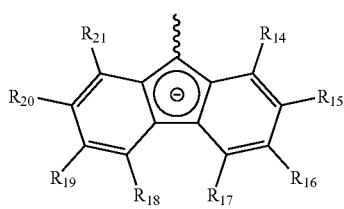

[Chemical Formula 3b]

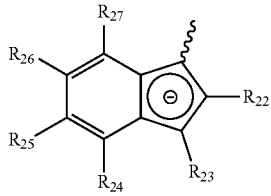

[Chemical Formula 3c]

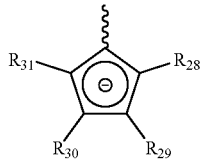

wherein, in Chemical Formulae 2a, 2b, 3a, 3b, and 3c, $R_1$ to $R_{31}$ and $R_{1'}$ to $R_{13'}$ are the same as or different from each other, and are each independently hydrogen, a halogen, a C1 to C20 alkyl group, a C1 to C20 haloalkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, provided that one or more of $R_9$ to $R_{13}$ and $R_{9'}$ to $R_{13'}$ are a C1 to C20 haloalkyl group, two or more neighboring groups of $R_{14}$ to $R_{31}$ are connected to each other to form a substituted or unsubstituted aliphatic or aromatic ring, and wherein B and M of Chemical Formula 1 are bonded to the cyclopentadienyl groups of $C_1$ and $C_2$ of Chemical Formula 1.

2. The metallocene compound of claim 1, wherein $R_1$ to $R_{31}$ and $R_{1'}$ to $R_{13'}$ in Chemical Formulae 2a, 2b, 3a, 3b, and 3c are each independently hydrogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, an ethoxy group, or a fluoroalkyl group.

3. The metallocene compound of claim 1, wherein $Q_1$ and $Q_2$ in Chemical Formula 1 are each independently hydrogen, a methyl group, an ethyl group, a propyl group, an isopropyl group, an n-butyl group, a tert-butyl group, a methoxymethyl group, a tert-butoxymethyl group, a tert-butoxyhexyl group, a 1-ethoxyethyl group, a 1-methyl-1-methoxyethyl group, a tetrahydropyranyl group, or a tetrahydrofuranyl group.

4. The metallocene compound of claim 1, wherein the compound represented by Chemical Formula 2a has the following structural formula:

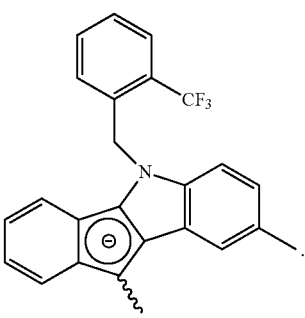

5. The metallocene compound of claim 1, wherein the compound represented by Chemical Formula 2b has the following structural formula:

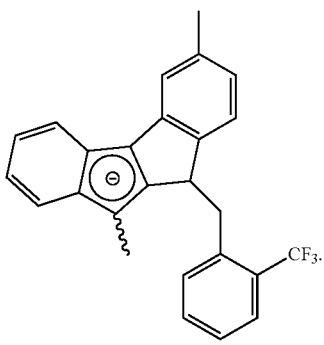

6. The metallocene compound of claim 1, wherein the compound represented by Chemical Formula 3a is any one of the following structural formulae:

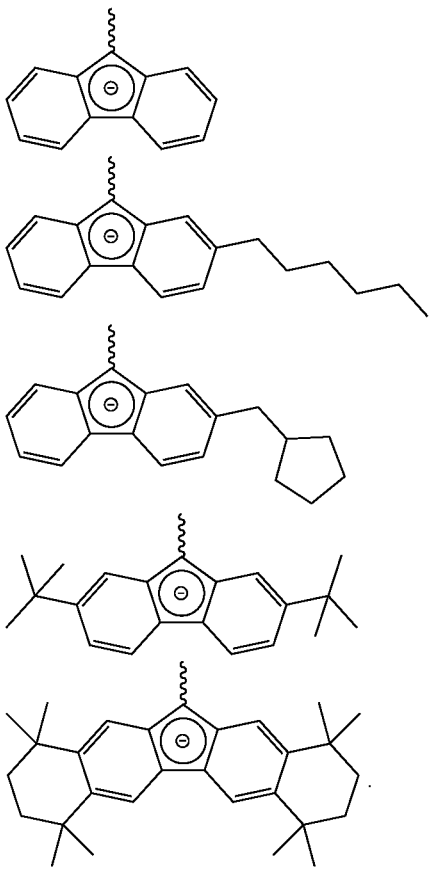

7. The metallocene compound of claim 1, wherein the compound represented by Chemical Formula 3b has the following structural formula:

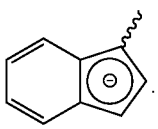

8. The metallocene compound of claim 1, wherein the compound represented by Chemical Formula 3c has the following structural formula:

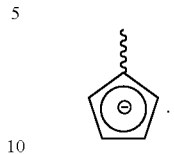

9. The metallocene compound of claim 1, wherein the compound represented by Chemical Formula 1 has the following structural formula:

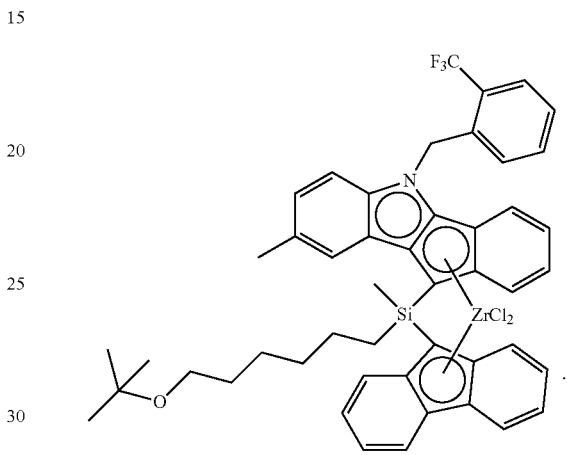

10. A catalyst composition comprising the metallocene compound of claim 1 and a cocatalyst.

11. The catalyst composition of claim 10, wherein the cocatalyst comprises one or more of compounds represented by the following Chemical Formula 4, Chemical Formula 5, and Chemical Formula 6:

$$—[Al(R_{32})—O]_n—$$ [Chemical Formula 4]

wherein, in Chemical Formula 4,
each $R_{32}$ may be same or different from each other, and is independently a halogen; a hydrocarbon having 1 to 20 carbon atoms; or a halogen-substituted hydrocarbon having 1 to 20 carbon atoms; and
n is an integer of 2 or more, $$J(R_{32})_3$$ [Chemical Formula 5]

wherein, in Chemical Formula 5,
$R_{32}$ is same as defined in Chemical Formula 4; and
J is aluminum or boron, $$[E-H]^+[ZA'_4]^- \text{ or } [E]^+[ZA'_4]^-$$ [Chemical Formula 6]

wherein, in Chemical Formula 6,
E is a neutral or cationic Lewis acid;
H is a hydrogen atom;
Z is a Group 13 element; and
each A' may be same or different, and is independently an
  aryl group having 6 to 20 carbon atoms or an alkyl group having 1 to 20 carbon atoms, of which one or more hydrogen atoms are unsubstituted or substituted with a halogen, a hydrocarbon having 1 to 20 carbon atoms, alkoxy, or phenoxy.

12. The catalyst composition of claim 10, wherein the catalyst composition is in the form of being supported on a support.

13. The catalyst composition of claim 12, wherein the support is one or more selected from the group consisting of silica, silica-alumina, and silica-magnesia.

14. A method of preparing a polyolefin, comprising the step of polymerizing olefin-based monomers in the presence of the catalyst composition of claim 10.

15. The method of claim 14, wherein the polymerizing is carried out by a solution polymerization process, a slurry process, or a gas phase process.

16. The method of claim 14, wherein the olefin-based monomer comprises one or more monomers elected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-eicosene.

\* \* \* \* \*